(12) United States Patent
Sander et al.

(10) Patent No.: US 6,335,039 B1
(45) Date of Patent: Jan. 1, 2002

(54) PHARMACEUTICAL FORMULATIONS COMPRISING VEGETAL MATERIAL SELECTED FROM TRICHILIA

(75) Inventors: Paulo Cezar Sander; Eduardo Augusto Moreira, both of Curitiba; Tadafissa Fujii, Joinville; Zulma Raquel Vaz, Joinville; Celso Shizuo Mizubuti, Joinville; Roberto Mikio Kassuya, Joinville; Andrea Bollmann, Joinville; Aldo Piazera Junior, Joinville; João Batista Calixto, Florianópolis, all of (BR)

(73) Assignee: Laboratorio Catarinense S/A, Joinville (BR)

( * ) Notice: Subject to any disclaimer, the term of this patent is extended or adjusted under 35 U.S.C. 154(b) by 0 days.

(21) Appl. No.: 09/462,357

(22) PCT Filed: Jul. 31, 1997

(86) PCT No.: PCT/BR97/00039

§ 371 Date: Mar. 28, 2000

§ 102(e) Date: Mar. 28, 2000

(87) PCT Pub. No.: WO99/02172

PCT Pub. Date: Jan. 21, 1999

(30) Foreign Application Priority Data

Jul. 10, 1997 (BR) ............................................. 9703946

(51) Int. Cl.[7] ...................... A61K 35/78; A61K 39/385; A01N 65/00

(52) U.S. Cl. ...................... 424/775; 424/725; 514/906; 514/929

(58) Field of Search ................................ 424/195.1, 775, 424/725; 514/929, 906, 931

(56) References Cited

FOREIGN PATENT DOCUMENTS

BE 829459 A * 11/1975

OTHER PUBLICATIONS

Fupi, V.W.K. and Moerk, P.C. Mafura nut oil and meal: processing and purification. 1982. JAOCS, J. Am. Oil Chem. Soc. 59, 94–98.*

Jolad, S., Hoffmann, J.J., Schram, R.H., Cole, J.R., Tempesta, M.S. and Bates, B. Constituents of *Trichilia hispida*. 1981. J. Org. Chem. 46, 4085–8.*

Nakatani, M., James, J.C., Nakanishi, K. Isolation and structures of trichilins, antifeedants the Southern army worm. 1981. J. Amer. Chem. Soc. 103, 1228–30.*

Zulma R. Vaz et al., "Analgesic Effect of The Herbal Medicine Catuama in Thermal and Chemical Models of Nociception in Mice", Phytotherapy Research, vol. 11, No. 2, Mar. 1997, pp. 101–106.

Joao B. Calixto et al., "Herbal Medicine Catuama Induces Endothelium–Dependent and Independent Vasorelaxant Action on Isolated Vessels From Rats, Guinea–Pigs and Rabbits", Phytotherapy, vol. 11, No. 1, Feb. 1997, pp. 32–38.

W.S. Garcez et al., "Sesquiterpenes from Trichilia Catigua", Fitoterapia, vol. 68, No. 1, 1997, pp. 87–88.

* cited by examiner

Primary Examiner—Thurman K. Page
Assistant Examiner—Liliana Di Nola-Baron
(74) Attorney, Agent, or Firm—Smith, Gambrell & Russell, LLP

(57) ABSTRACT

The present invention refers to a method for producing vasodilation or analgesia in a mammal, comprising the use of vegetal material derived from the bark of a Trichilia species.

4 Claims, 5 Drawing Sheets

PHARMACEUTICAL FORMULATIONS COMPRISING VEGETAL MATERIAL SELECTED FROM TRICHILIA

FIELD OF THE INVENTION

The present invention refers to the use of vegetal material selected from Trichilia for the preparation of pharmaceutical compositions.

BACKGROUND OF THE INVENTION

Medicinal plants known as catuaba have recognized pharmaceutical use due to its aphrodisiac activities, as a tonic and in the treatment of physical and mental fatigues.

Phytotherapic formulations prepared from such plants extracts are already known from the prior art, in which these specific extracts may used alone or in association with other medicinal plant extracts, such as the Brazilian shrub (*Paullinia cupana*). Several alternative formulations comprising extracts from other catuaba species have already been disclosed in the art, all of them being related to the tonic activity of this particular group of plants.

SUMMARY OF THE INVENTION

The present invention refers to the use of vegetal material selected from Trichilia for the preparation of pharmaceutical formulations showing vasodilating and analgesic activities.

In another aspect the present inventions is directed to pharmaceutical compositions presenting vasodilating, analgesic or sexual stimulating activities comprising a vegetal material selected from Trichilia as the active ingredient.

DETAILED DESCRIPTION OF THE INVENTION

Figure 1:
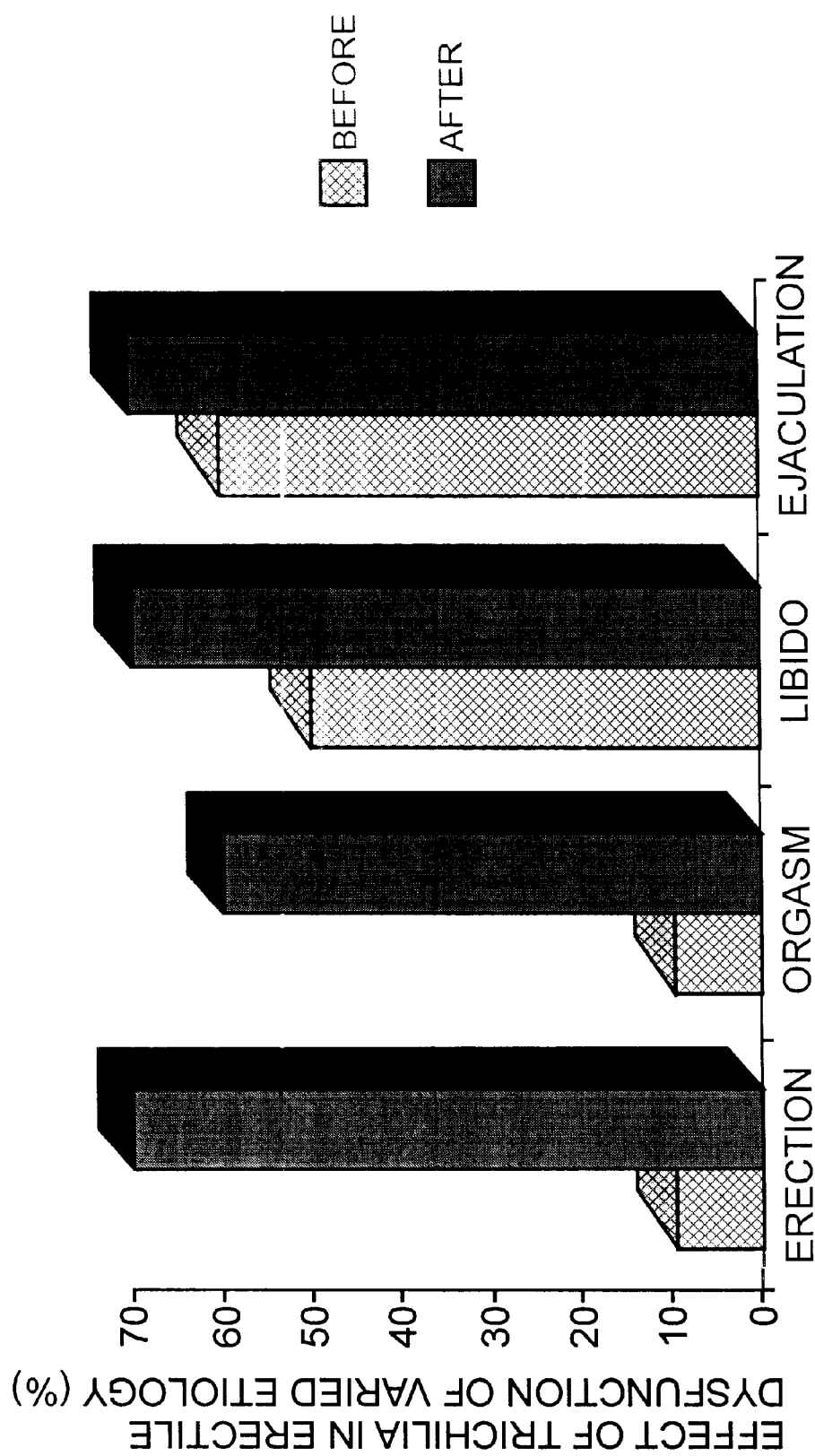
FIG. 1 shows the effect of treatment with a Trichilia extract of male patients suffering from functional sexual incapacity of varied etiology.

After detailed studies, the inventors found out that one particular plant of the group of catuaba, Trichilia sp., has surprising analgesic and vasodilating activities due to its vasorelaxant effect. It has been found that *Trichilia catigua*, for example, is able produce vasodilating effects in thoracic aorta and in pulmonary and mesenteric arteries of rodents.

Although up to this moment there is no scientific corroboration of the exact mechanism which produces the above effect, evidences lead to the conclusion that the vasorelaxant activity of an Trichilia sp. extract depends upon the presence or absence of endothetium in blood and lymphatic vessels. In this event, the above mentioned effect would be associated to the release of nitric oxide (NO) or a NO-mediated substance in the endothelium. Tests carried out in rats' aortas, for example, showed that the vasorelaxation action of a Trichilia sp. extract was partially reduced when the vascular endothelium had been removed. In an additional experiment, the incubation of aorta, pulmonary and mesenteric arteries of rats, rabbits and guinea-pigs with the selective NO-synthase inhibitor L-NOARG, N-nitro-L-arginine, significantly antagonized the vasorelaxation effect caused by Trichilia extract. In a further assay, the inventors verified that the use of methylene blue which is an inhibitor of soluble guanylate cyclase activated by NO (Gruetter et al., 1981) partially affected the vasorelaxant action of Trichilia sp. in rings extracted from pulmonary arteries.

Taken together, the results of the above cited studies show that the vasorelaxation actions of a vegetal material from Trichilia sp. is mediated both by endothelium-dependent and -independent mechanisms.

Due to the unexpected vasorelaxant activity of Trichilia sp., the present inventors found out that extracts thereof also show an analgesic effect.

Tests carried out in chemical models of pain stimulation in mice, for example, demonstrated a strong analgesic action of Trichilia extracts. Experimental results showed that this vegetal extract significantly inhibits the nociceptive effect induced by the chemical agent—acetic acid 0.6% v/v. The material extracted from Trichilia produced a significant and long lasting analgesic effect in the nociceptive condition in accordance with the previously mentioned model and such analgesic effect may last up to 6 hours. On the other hand, additional tests carried out with Trichilia extracts in association with other plant extractive products demonstrated that when the animals are previously treated (10 minutes before the main administration) with naloxone (a non-selective opioid antagonist), the analgesic action of morphine as well as of a Trichilia containing formulation has been reverted in the acute and inflammatory phases of pain induced by formalin at 2.5% w/v as the chemical agent.

As occurs in its vasorelaxation action, the actual mechanism through which Trichilia provides an analgesic effect is not totally explained yet but it seems to involve, at least partially, an interaction with the opoid system. However, a deep analysis of the results obtained with the invention indicates that vegetal extracts of this particular catuaba species present excellent effects in the treatment of pain alleviation.

An advantage of the present invention lays on the fact that, in contrast to what occurs, for example, with non-steroidal anti-inflammatory drugs, such as acetylsalicylic acid, Trichilia is effective in the initial (acute) phase of certain nociceptive conditions as it can be observed in nocicepptive conditions induced by formalin and capsaicin.

Still another advantage of the present invention refers to the absence of toxic effects caused by the vegetal material extracted from Trichilia sp. Tests carried out in mice, for example, clearly showed the lack of toxicity in the administration of Trichilia sp. extracts, alone or in association with other plants extracts, even in high doses under acute or subcronic forms, in daily doses up to 1 g/kg. This observation could also be verified in human beings in dosages of 25 mL twice a day for four weeks.

Still in a further aspect, the present invention refers to the use of a vegetal material selected from Trichilia sp. for the treatment of functional sexual incapacity of varied etiology, liable to be clinically treated. A clinical test has been made in 14 male patients suffering from functional sexual incapacity of varied etiology who were subjected to a treatment with a liquid formulation comprising from 0.50 to 5.00% wt. of Trichilia sp. extract for 30 consecutive days demonstrated significant clinical recovery when evaluated for typical features of the syndrome such as erection, orgasm, libido and ejaculation. The results are shown in FIG. 1. These results are supported by the pharmacological characterization of the dose-dependent vasorelaxant activity induced by the formulation containing vegetal material selected from Trichilia in isolated segments of the corpus cavernosum both of rabbits and human beings. A complementary evaluation of probable mechanisms for this particular activity should encompass the verification of the possibility of it to be involved with the ionic channels linked to the membrane of that tissue.

Therefore, the present invention is related to the vasoactive, analgesic and vasorelaxant activities of extracts of Trichilia and of formulations containing same as the active ingredient in connection with corpus cavernosum of vessels. In view of the proportionality of each of such activities in the final result due to the natural variability of the vegetal material and the dependence of the specific technological process applied for obtaining and transforming same, there may still be a functional inter-relationship among those activities. Thus, it is assumed that there is a contribution of the vasorelaxant effect in the analgesic activity based on a better component distribution of the constituents present in the vegetal material probably involved in the biological mediation. On the other hand, there is a possible relationship of the analgesic action of Trichilia, particularly the one provided in the inflammatory phase of pain chemical induction, with the vasorelaxant effect mediated by the substances which take part in the inflammatory process, such as those analogous to cinines and prostaglandines.

The inventors have found out that any plant of the genus Trichilia, such as *T. catigua A. Juss, T. clausseni C. DC., T. casaretti C. DC., T. pallida Swartz.* and *T. elegans A. Juss*, may be useful for the objectives of the present invention. It has been verified that among the above cited species, the Trichilia catigua is particularly preferred. Moreover, the vegetal material extracted from Trichilia sp. used in the present invention is preferably barks which are advantageously employed as alcoholic extracts and, more preferably, are formulated with inert pharmaceutically acceptable carries. Trichilia sp. formulations useful for the present invention may be, for example, orally administered in the form of tablets, coated tablets, soft and hard gelatin capsules, solutions, emulsions and suspensions, or rectally administered in the form of suppositories. Suitable carriers include, but are not restricted to, lactose, starch or its derivatives, talc, stearic acid or the salts thereof in the case of solid formulations for oral administration. Carriers suitable for soft gelatin capsules, on the other hand, include vegetal oils, waxes, fats, liquid and semi-solid polyols. Solutions may be prepared by using carriers selected from the group comprising water, carbohydrates and polyols. For suppositories appropriated carriers comprise natural or hardened oils, waxes, fats and polyols.

In addition to the pharmaceutical carriers, the Trichilia sp formulations in accordance with the present invention may also contain additives such as conservation agents, solubilizers, stabilizers, wetting agents, emulsifiers, sweeteners, dyers. flavoring agents, tonicity adjust aids, buffers, coating agents and antioxidants. They may still comprise additional compatible active ingredients in the event it is desirable to enhance the vasodilating or analgesic action, or if further therapeutic effects are also intended.

In order to obtain the appropriate vasodilating or analgesic effects, the necessary dosage of Trichilia sp. will, of course, depend upon each particular case and may, therefore, vary in a wide range, being not a determinant parameter of the present invention. However, it has been observed that an effective dosage for oral administration in human beings may vary in a range corresponding to 10 mg to 0.5 g of Trichilia sp. extract per day. In the event pharmaceutical formulations containing the extract of Trichilia sp are used, the intended results may be effectively obtained by employing concentrations of 0.2 to 50% wt. of the cited extract based on the total formulation.

The following illustrative examples will be useful better to demonstrate the present invention. It should be, however, noted that the following illustrative data and procedures merely refer to some possible embodiments of the invention which should not be taken as limiting parameters of the scope thereof.

EXAMPLES

Preparation of an Alcoholic Extract of Trichilia catigua 500 g of *Trichilia catigua* barks were extracted with an 1:1 (v/v) water-ethanol solution at room temperature for 7 days. The resulting extract was, then, filtered and concentrated using a rotavapor under 40 mmHg at 60° C. The extract was maintained under refrigeration until use.

Preparation of Pharmaceutical Formulations

The *Trichilia catigua* alcoholic extract obtained as described above was used to prepare the formulations set forth below:

| Component | % wt. |
| --- | --- |
| Liquid Formulation (I) | |
| extract of Trichilia | 0.50 a 5.00 |
| extracti of Muirapuama | 0.10 a 2.00 |
| extract of Gengibre | 0.01 a 0.20 |
| extract of Guaraná | 0.10 a 2.00 |
| suitable carrier | 90.80 a 99.29 |
| Solid Formulation (II) | |
| extract of Trichilia | 5 a 50 |
| extract of Muirapuama | 2 a 15 |
| extract of Gengibre | 0.2 a 2 |
| extract of Guaraná | 2 a 15 |
| suitable carrier | 18 a 90.80 |

Vasorrelaxant Activity Assay (a) In Isolated Thoracic Aorta

Thoracic aortas isolated from male Wistar rats (250 g–350 g) were cleaned of connective tissue and adherent fat, without damaging the endothelium, cut into rings of about 2–3 mm wide and suspended in a 5 mL organic bath chamber containing Krebs-Hanseleit solution at 37° C., pH 7.2, gassed with 95% $O_2$ and 5% $CO_2$ at pH 7.4. For some experiments the vascular endothelium was removed by gently rubbing the internal surface of the artery with a wooden stick. Endothelium integrity was functionally determined by evaluating the ability of acetylcholine (Ach 1 $\mu$M) to produce relaxation of samples precontracted with noradrenaline (NA, 1–100 nM). The samples were considered as having a viable endothelium when Ach evoked relaxations of 60% and were considered as being endothelium denuded when Ach failed to cause relaxation (as described in Furchgott and Zawadski, 1980).

Samples were submitted to a basal tension of 1 g and were allowed to equilibrate for at least 90 min prior to addition of any drug, the bath solution being renewed every 20 min during this time period. Isometric tension changes were recorded by means of a F-60 force-transducer (Narco Biosystems or Letica 6006). The submaximal contractile responses in the samples induced by noradrenaline were taken as the 100% values and all subsequent responses were calculated as a percentage of this value.

Following the equilibration period, samples were contracted by addition of noradrenaline (NA) (100 nM) and once the tonic responses became stable (usually after 5 min), an alcoholic extract of *Trichilia catigua* as previous prepared was cumulatively added both to the rings provided with endothelium and to those from which the endothelium had been removed, at concentrations from 1 to 3000 µg/mL. Prior to its utilization, the extract of *Trichilia catigua* was diluted until the alcohol concentration did not exceed 0.05% v/v in the nutrition medium.

The results of the cumulative addition of the extract of *Trichilia catigua* did not show any effect in the tonus of the biological preparations, but produced a vasodilating response both in the aorta rings with intact endothelium and in the rings free from endothelium. The results are shown in Table 1:

TABLE 1

Effect of vegetal extract of Trichilia in aorta rings from rats

| Vegetal Material | aorta rings of rats | |
|---|---|---|
| | with endothelium $E_{max}(\%)$ | without endothelium |
| T. catigua | 86.0 ± 7.1 | 28.0 ± 3.4 |

$E_{max}(\%)$ - Maximum Effect (%)

(b) In Isolated Pulmonary and Mesenteric Arteries

Isolated mesenteric and pulmonary arteries from guinea-pigs (400 g–450 g) and rabbits (2 Kg–3 Kg) of both sexes were cleaned of connective tissue and adherent fat, without damaging the endothelium, cut into rings of about 2–3 mm wide and treated in the same way describe in item (a) above.

Samples were submitted to a basal tension of 2–4 g, were allowed to equilibrate for at least 90 min prior to addition of any drug, the bath solution being renewed every 20 min during this time period, and further treated as indicated in item (a) above.

The results of the cumulative addition of the extract of *Trichilia catigua* did not show any effect in the tonus of the biological preparations, but produced a vasodilating response in the pulmonary and mesenteric rings both with intact endothelium and without endothelium.

Analgesic Activity Assays

Male Swiss mice varying from 25 to 35 g, were housed at 22° C.±2° C. under a 12 h light/12 h dark circle and with access to water and purina. The animals were acclimatized to the laboratory for at least 1 hour before testing and were used once throughout the experiments.

Analgesia Assay (a) Acetic Acid-induced Abdominal Constriction

The abdominal constriction induced by acetic acid injections (6.0% v/v) consists of the contraction of abdominal muscle together with the stretching of hind limbs. Animals were pretreated with 200 mg of an alcoholic extract of *Trichilia catigua* 6 hours prior to the experiment. Control animals received a similar volume of a 0.90% NaCl solution (10 mL/Kg). After challenge to the acetic acid, pairs of mice were placed in separate boxes and the number of abdominal constrictions was cumulatively counted over a period of 20 minutes. Antinociception was expressed as the reduction of abdominal constrictions between control animals treated with the saline solution and mice pretreated with the Trichilia extract.

A composition comprising an extract of *T. catigua* associated with other vegetal extractive materials as set forth in formulation (I) previously cited was tested in rats following the same procedure mentioned above. The results are indicated in Table 2:

TABLE 2

Analgesic Effect of Trichilla Vegetal Extractive Material in Nociception Induced by Acetic Acid

| Vegetal Material | Nociception by Acetic Acid $I_{max}(\%)$ |
|---|---|
| T. catigua | 82.0 ± 2.0 |
| Formulation with T. catigua (I) | 70.0 ± 2.0 |

$I_{max}(\%)$ - Maximal Inhibition (%)

The data contained in the above table shows that the alcoholic extract of *Trichilia catigua* administrated alone or in a formulation in which it is associated with other vegetal extractive materials caused a significant reduction of abdominal constrictions induced by acetic acid.

Formulation (I) comprising several vegetal extracts was additionally tested following the above procedure, but employing pretreatment administrations of 1 to 24 hours prior to the challenge to acetic acid. The results are shown in Table 3:

TABLE 3

Time-dependent Analgesic Effect of Extractive Formulation (I) of Trichilia in the Nociception Induced in Mice by Acetic Acid

| Time (h) | Nociception by Acetic Acid $I_{max}(\%)$ |
|---|---|
| 1 | 29.6 ± 2.5 |
| 2 | 34.8 ± 1.5 |
| 4 | 57.8 ± 1.9 |
| 6 | 70.0 ± 2.0 |
| 8 | 43.2 ± 4.4 |
| 10 | 8.3 ± 2.1 |
| 12 | 3.8 ± 1.5 |
| 24 | 3.8 ± 2.9 |

$I_{max}(\%)$ - Maximal Inhibition (%)

(b) Formalin-induced Licking

Mice were lightly anaesthetized, with exception of those used to analyze the first phase of fromalin-induced pain. The surface of the animals paws was injected with 20 µL of 2.5% w/v formalin. Two groups of mice (mice treated with *T. catigua* and control mice) were simultaneously observed over a period from 0 to 30 min after the formalin injection. The total time spent by the animal licking the injected paw was timed with a chronometer and was considered as an indicative of pain. The first phase of the nociceptive response normally occurred after 5 min after the formalin injection and the second phase was from 15 to 30 min after such induction. These phases represent the neurogenic and inflammatory responses, respectively. In order to avoid pharmacokinetic influences, different groups of animals were used to analyze each phase of the experiment. Alternatively, animals were pretreated with naloxone 10 min prior to the administration of compositions comprising an extract of *T. catigua*. The obtained data is indicated in Table

4:

TABLE 4

Antinociceptive Effect of Vegetal Extract of Trichilia in Pain Induced in Mice by Formalin

| Vegetal Material | nociception by formalin | |
|---|---|---|
| | 0–5 min. | 15–30 min |
| | $I_{max}(\%)$ | |
| T. catigua | 32.0 ± 3.0 | 35.0 ± 10.0 |

$I_{max}(\%)$ - Maximal Inhibition (%)

Superfusion of Isolated Corpus cavernosum

Corpus carvenosum tissue isolated from penis of New Zealand rabbits and adult men, cleaned of connective tissue and albuginic tunic was dissected into segments of 2–3 cm wide. The samples were placed in cascade form, under tension of 2.5 g, superfused in nutritive Krebs-Ringer solution at 37° C. and pH of 7.2, gassed with 95% $O_2$ and 5% $CO_2$ at pH 7.4. The tissues were attached to auxotonic handles connected to isotonic transducers (Harvard) for smooth muscles. The responses were registered in a multi-channel polygraph (Watanabe, WR 3101). Samples were stabilized for at least 90 min and the tissue tonus were induced by a continuous infusion (0.1 mL/min) of NA (3 $\mu$M) or KCl (35 mM). In this experiment, the agonists were administrated as a bolus (10–100 $\mu$L) while the antagonists and inhibitors were administrated by continuous infusion (0.1 mL/min) for about 20 min prior to the administration of formulation (I) comprising extractive material from *Trichilia catigua*. The results are indicated in FIGS. 2 to 5.

Figure 2:
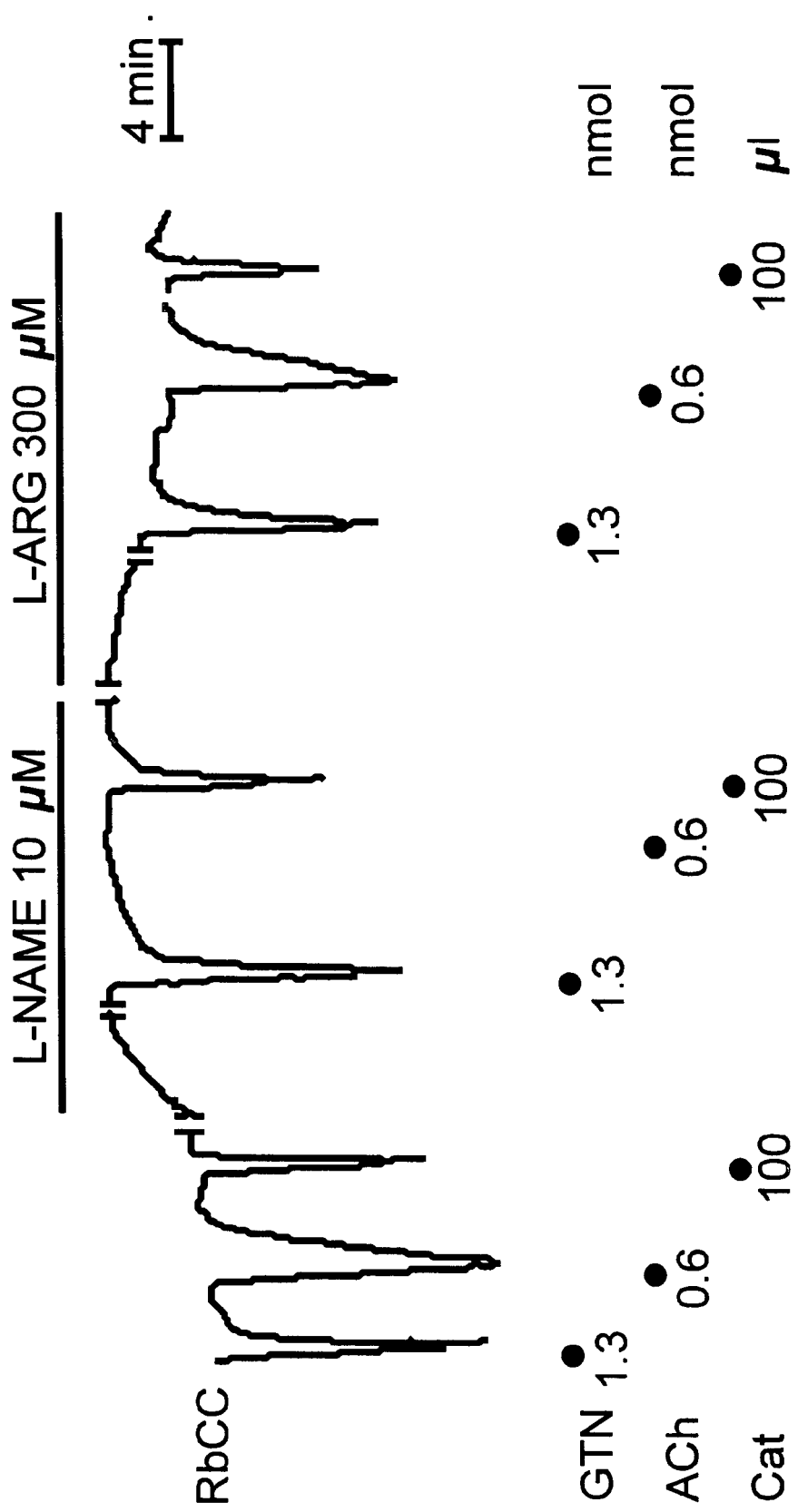
FIG. 2 shows the effect of L-NAME and L-Arg on basal tonus and relaxation of the corpus carvernosum tissue of rabbits (RbCC)

FIG. 2 shows that the infusion of L-NAME ($N^\omega$-nitro-L-arginine methyl ester, 10 $\mu$M) enhanced the basal tonus of the corpus cavernosum of the rabbit (RbCC) and inhibited the relaxation induced by acetylcholine (ACh). Relaxations evoked by glyceryltrinitrato (GTN), and by the composition containing a vegetal material selected from Trichilia as the active ingredient (Cat) were not affected by the L-NAME infusion. The subsequent infusion of L-arginine (L-arg, 300 $\mu$M) reverted the enhanced tonus and restored the relaxation induced by Ach. The experimental data indicated in FIG. 2 is representative of 6 experiments.

Figure 3:
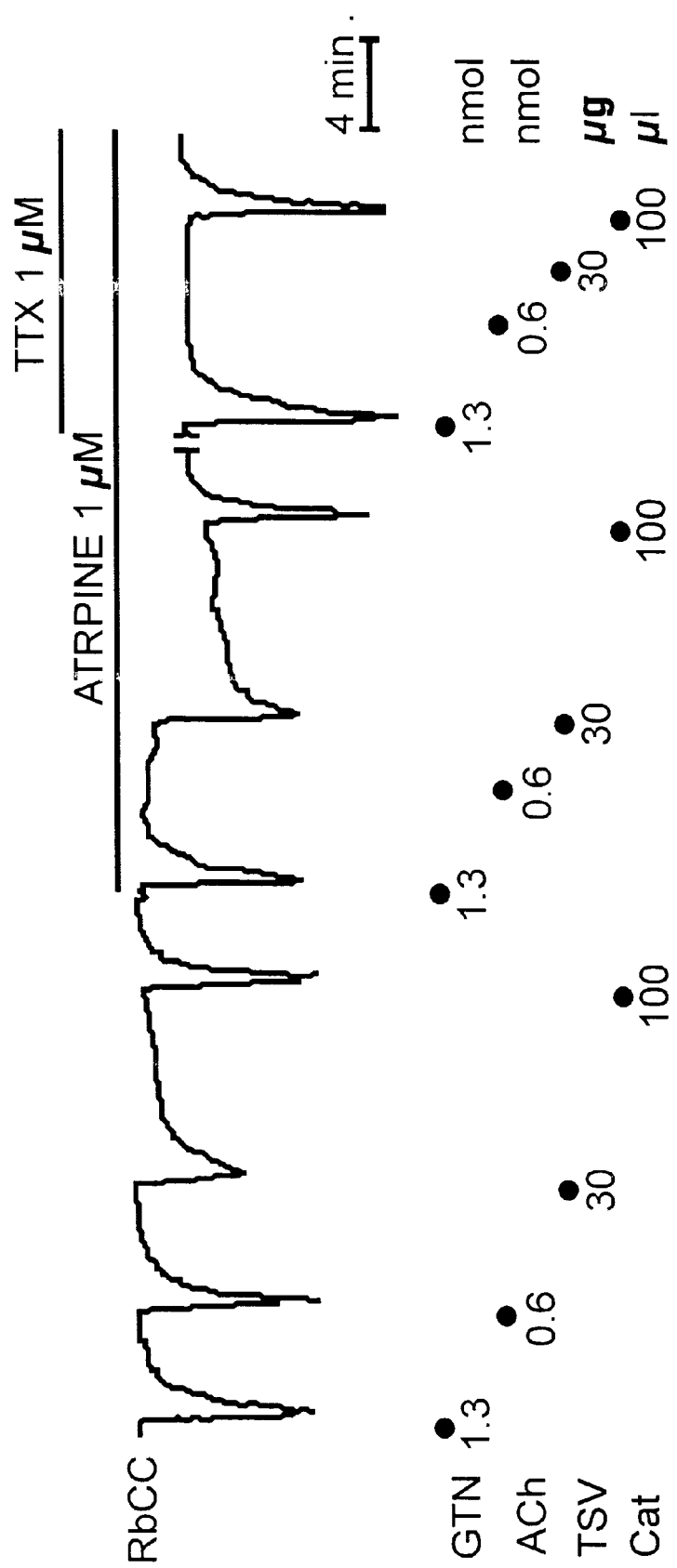
FIG. 3 shows the effect of Atropine and TTX on RbCC basal tonus and relaxation.

FIG. 3, on the other hand, shows that the antagonist of muscarinic receptors, atropine (1 $\mu$M) and sodium channel blockers, tetrodotoxin (TTX, 1 $\mu$M), did not present any effect on the relaxation of rabbits' corpus cavernosum (RbCC) induced by a composition containing a vegetal material selected from Trichilia as the active ingredient (Cat) and by glyceryltrinitrate (GTN). However, relaxations evoked by the acetylcholine (Ach) and by poison of *Tityus serrulaus* (TSV) were abolished by atropine and tetrodotoxin, respectively. The experimental data indicated in FIG. 3 is representative of 4 experiments.

Figure 4:
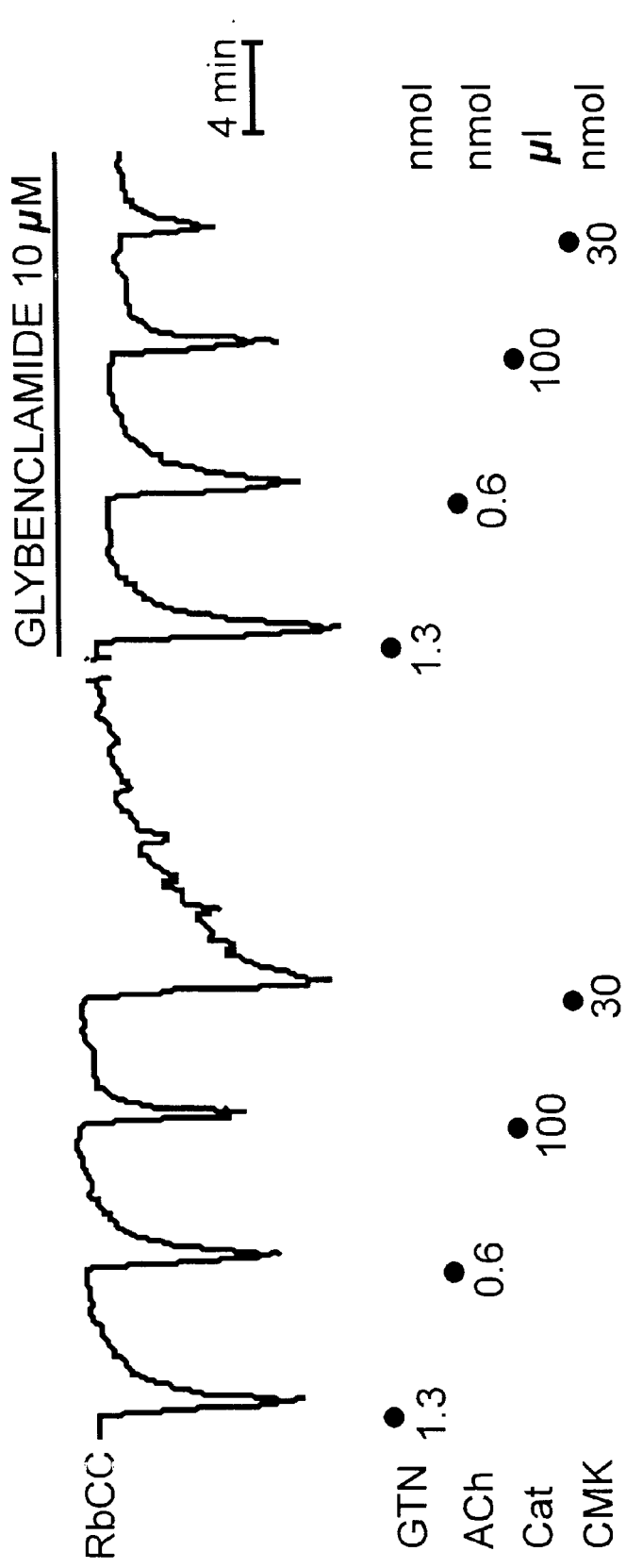
FIG. 4 shows the effect of Glybenclamide on RbCC basal tonus and relaxation.
Figure 5:
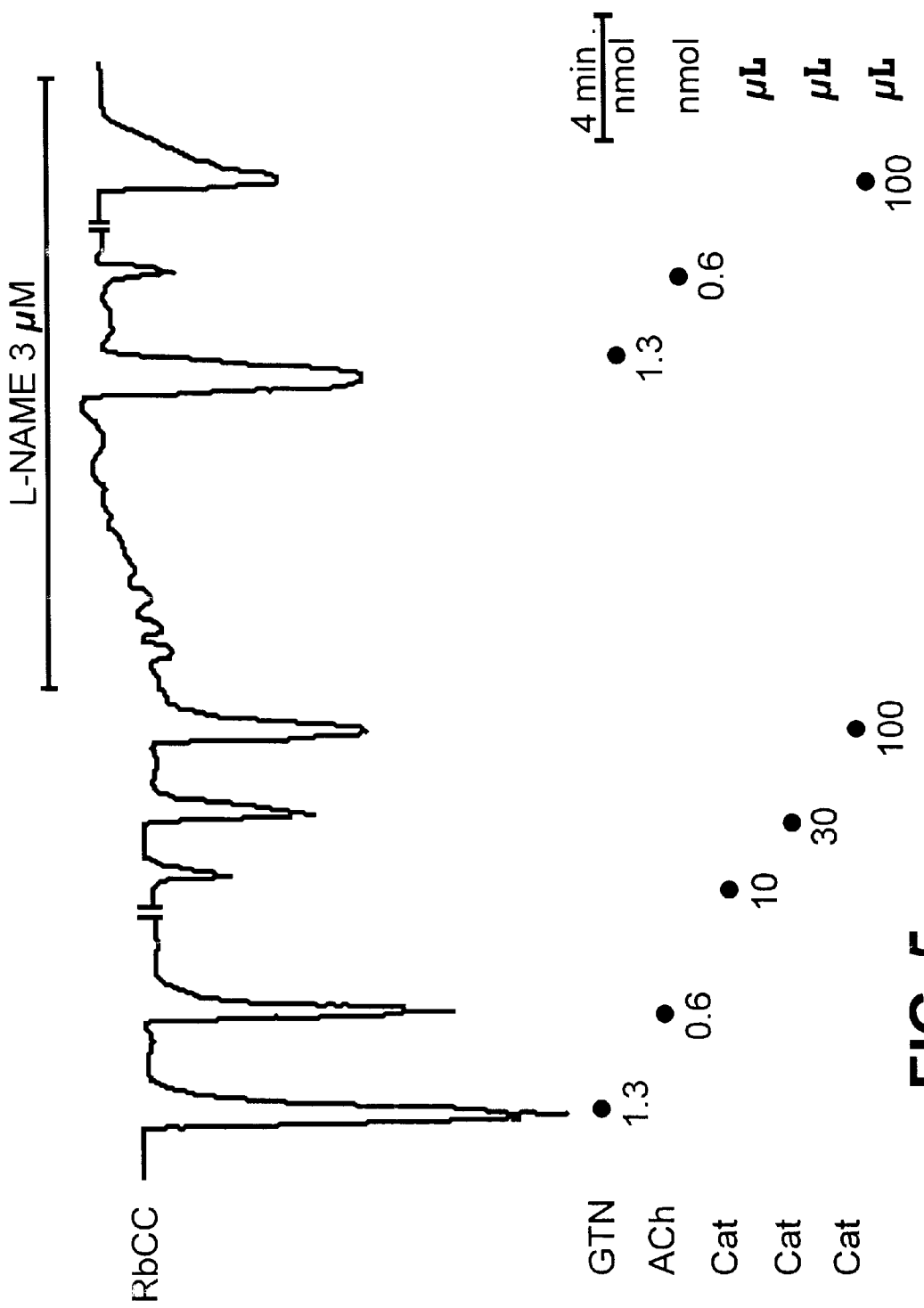
FIG. 5 shows the effect of L-NAME on HCC basal tonus and relaxation.

In FIG. 4 it is possible to observe that the ATP-dependent potassium channel blocker (10 $\mu$M) inhibited the relaxation of the rabbit cavemous body (RbCC) induced by cromakalim (CMK) without affecting the relaxation induced by acetylcholine (Ach), by glyceryltrinitrate (GTN) and by the composition containing a vegetal material selected from Trichilia as the active ingredient (Cat). The infusion of L-NAME enhanced the HCC tonus and significantly reduced the relaxation induced by Ach (0.6 $\mu$M). The relaxations induced by GTN (1.3 $\mu$M) and the composition contain a vegetal material selected from Trichilia as the active ingredient (Cat, 10–100 $\mu$L) were not significantly affected by the L-NAME infusion. For these tests 4 tissue strips obtained from 2 donators were used.

What is claimed is:

1. A method of producing vasodilation or analgesia in a mammal, comprising:

administering to a mammal in need of such treatment an amount of a composition, derived from bark of a Trichilia species selected from the group consisting of *T. catigua A. Juss., T. clausseni C. DC., T. casaretti C. DC., T. pallida Swartz,* and *T. elegans A. Juss.*, sufficient to induce a vasorelaxant effect.

2. The method according to claim 1, wherein the Trichilia species is *Trichilia catigua.*

3. The method according to claim 1, wherein the composition derived from a Trichilia species is a vegetal material in the form of an alcoholic extract.

4. The method according to claim 1, wherein the Trichilia species is a member selected from the group consisting of *T. catigua, T. clausseni, T. casaretti, T. pallida,* and *T. elegans.*

* * * * *